United States Patent [19]

Majoie et al.

[11] Patent Number: 4,528,294
[45] Date of Patent: Jul. 9, 1985

[54] BENZOYL-PHENYL-PIPERIDINE DERIVATIVES

[75] Inventors: Bernard Majoie, Dijon; François Bellamy, Saulon-La-Rue; Pierre Dodey; Jacques Robin, both of Dijon, all of France

[73] Assignee: Societe de Recherches Industrielle S.O.R.I., Paris, France

[21] Appl. No.: 391,915

[22] Filed: Jun. 24, 1982

[30] Foreign Application Priority Data

Jun. 29, 1981 [FR] France ................................. 81 12745

[51] Int. Cl.³ .................... A61K 31/445; C07D 295/12
[52] U.S. Cl. ..................................... 514/327; 546/235; 546/234; 546/237; 546/217; 546/220; 546/221; 514/328; 514/331; 514/885
[58] Field of Search ............... 546/234, 235, 217, 220, 546/221; 424/267

[56] References Cited

U.S. PATENT DOCUMENTS

| | | | |
|---|---|---|---|
| 3,202,655 | 8/1965 | Metlesics et al. | 546/235 |
| 3,261,867 | 7/1966 | Fryer et al. | 546/235 |
| 3,668,199 | 6/1972 | Szmuszkovicz. | |
| 3,989,701 | 11/1976 | Toth et al. | 546/235 |
| 4,021,563 | 5/1977 | Hernestam et al. | |
| 4,064,121 | 12/1977 | Toth et al. | 546/235 |

FOREIGN PATENT DOCUMENTS

| | | |
|---|---|---|
| 1350325 | 12/1963 | France. |
| 1375300 | 9/1964 | France. |
| 1403939 | 5/1965 | France. |
| 1526708 | 4/1968 | France. |
| 1530393 | 5/1968 | France. |
| 2070102 | 9/1971 | France. |
| 2238480 | 2/1975 | France. |
| 2238483 | 2/1975 | France. |
| 2056447 | 3/1981 | United Kingdom. |

OTHER PUBLICATIONS

Loudon et al., J. Chem. Soc. (1954), pp. 1134–1137.
H. Möhrle et al., Arch. Pharm. (Weinheim) (1979), vol. 312, pp. 219–230.
C. V. T. Campbell et al., Jour. Chem. Soc. (1941), pp. 747–750.

Primary Examiner—Norma S. Milestone
Attorney, Agent, or Firm—Schwartz, Jeffery, Schwaab, Mack, Blumenthal & Evans

[57] ABSTRACT

The present invention relates to new benzoyl-phenyl-piperidine derivatives selected from the group consisting of:
(i) 2-piperidinobenzophenones of the general formula:

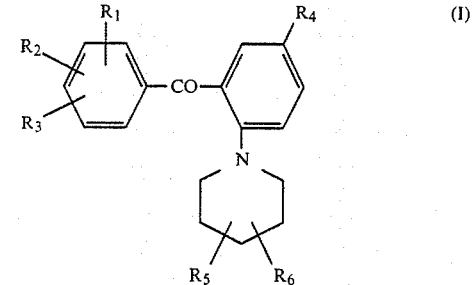

in which:
$R_1$, $R_2$ and $R_3$, which are identical or different, each represent an atom of hydrogen, a hydroxy group, $CF_3$, a halogen, a lower alkyl group or a lower alkoxy group;
$R_4$ represents an atom of hydrogen, a halogen, an $NO_2$ group, an $NR'R''$ group [where $R'$ and $R''$, which are identical or different, represent an atom of hydrogen, a lower alkyl group or a $CO_2R$ group (where R represents a lower alkyl group or a benzyl group)];
$R_5$ and $R_6$, which are identical or different, each represent an atom of hydrogen, a $C_1$–$C_4$-alkyl group, an OH group, a phenyl group or a benzyl group; and
(ii) acid addition salts thereof.

The invention also relates to the method for preparing these new derivatives and to their use in therapeutics, particularly as immunostimulant and immunoadjuvant agents.

5 Claims, No Drawings

BENZOYL-PHENYL-PIPERIDINE DERIVATIVES

The present invention relates as new industrial products to derivatives belonging to the family of the benzoyl-phenyl-piperidines, namely derivatives of 2-piperidinobenzophenone of formula I hereinafter. It also relates to the method for preparing same and to their application in therapeutics, particularly as immunostimulant and immunoadjuvant agents.

It is known that a certain number of benzoyl-phenyl-piperidine derivatives (which do not correspond to formula I hereinafter) has already been described. In particular, French Pat. Nos. 1 375 300 and 1 403 939 disclose the [2-(piperidinyl)-phenyl]-(2-amino-5-chlorophenyl)-methanone as intermediate product of synthesis in the preparation of benzodiazepines; French Pat. No. 1 350 325 discloses the [2-amino-5-(1-piperidinyl)-phenyl]-(phenyl)-methanone and [2-nitro-5-(1-piperidinyl)-phenyl]-(phenyl)-methanone as intermediate products of synthesis in the preparation of benzodiazepines; French Pat. No. 74 25070 (publication No. 2 238 480) and No. 74 25735 (publication No. 2 238 483) disclose the [3-amino-4-(1-piperidinyl)-phenyl]-(phenyl)-methanone and [3-nitro-4-(1-piperidinyl)-phenyl]-(phenyl)-methanone, recommending them as agents inducing the hepatic microsomal enzyme and antipyretic agents, and the Article by Loudon et al., J. Chem. Soc., 1954, pages 1134–1137 discloses [3,5-dinitro-2-(1-piperidinyl)-phenyl]-(phenyl)-methanone.

It has now been surprisingly found that new benzoyl-phenyl-piperidine derivatives, which are structurally different from the previously known products, are particularly interesting in therapeutics due to their immunological properties.

According to the invention, a new benzoyl-phenyl-piperidine derivative is recommended which is characterised in that it is selected from the group consisting of:

(i) 2-piperidinobenzophenones of the general formula:

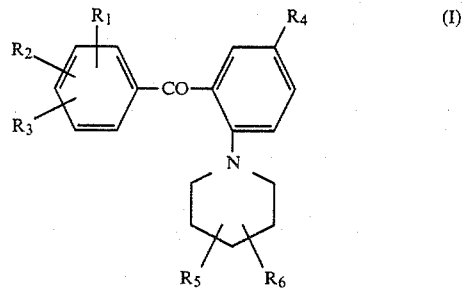

in which:

$R_1$, $R_2$ and $R_3$, which are identical or different, each represent an atom of hydrogen, a hydroxy group, $CF_3$, a halogen, a lower alkyl group or a lower alkoxy group;

$R_4$ represents an atom of hydrogen, a halogen, an $NO_2$ group, an $NR'R''$ group [where $R'$ and $R''$, which are identical or different, represent an atom of hydrogen, a lower alkyl group or a $CO_2R$ group (where R represents a lower alkyl group or a benzyl group)];

$R_5$ and $R_6$, which are identical or different, each represent an atom of hydrogen, a lower alkyl group, an OH group, a phenyl group or a benzyl group; and (ii) acid addition salts thereof.

Lower alkyl and lower alkoxy groups are understood here to mean a branched or straight hydrocarbon radical, containing from 1 to 4 atoms of carbon, such as for example the methyl, ethyl, n-propyl, isopropyl, n-butyl, isobutyl, tertiobutyl groups and the methoxy, ethoxy, n-propoxy, isopropoxy, n-butoxy, isobutyloxy and tertiobutyloxy groups.

Atom of halogen is understood here to mean an atom of chlorine, an atom of bromine or an atom of fluorine.

Acid addition salts are understood here to mean the addition salts obtained by reaction of a free base of formula I with an inorganic or organic acid. From the acids which are appropriate for this purpose, particular mention may be made of the hydrochloric, hydrobromic, sulphuric, phosphoric, acetic, fumaric, maleic, oxalic, citric, tartaric, lactic, malic, benzoic, succinic, phenylacetic, methanesulphonic, ethanesulphonic, paratoluenesulphonic acids.

Among the compounds of formula I according to the invention, the most advantageous products are those represented by formulae I' and I" hereinafter, namely:

(a) 2-piperidinobenzophenones of formula:

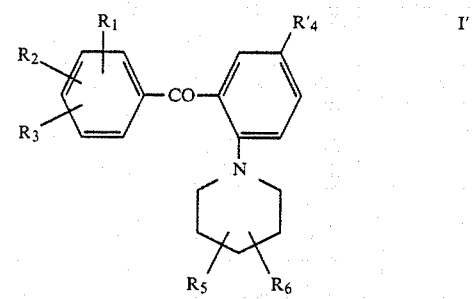

[in which $R_1$, $R_2$ and $R_3$, which may be identical or different, each represent H, F, Cl, Br, OH, $CF_3$, $C_1$–$C_4$-alkyl or $C_1$–$C_4$-alkoxy; $R'_4$ represents H, F, Cl, Br or $NR'R''$ where $R'$ and $R''$, which are identical or different, each represent H, $C_1$–$C_4$-alkyl or $CO_2R$ (where R is $C_1$–$C_4$-alkyl or benzyl); $R_5$ and $R_6$, which are identical or different, each represent H, $C_1$–$C_4$-alkyl, OH, $C_6H_5$ or $C_6H_5CH_2$] and acid addition salts thereof; and (b) 2-piperidinobenzophenones of formula:

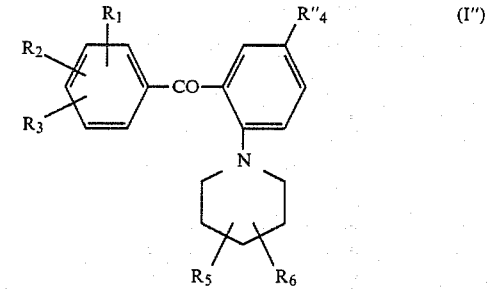

[in which $R_1$, $R_2$ and $R_3$, which may be identical or different, each represent H, F, Cl, Br, OH, $CF_3$, $C_1$–$C_4$-alkyl or $C_1$–$C_4$-alkoxy; $R''_4$ represents H, F, Cl, Br, $NO_2$ or $NR'R''$ (where $R'$ and $R''$ are defined as indicated hereinabove); $R_5$ and $R_6$, which are identical or different, each represent H, $C_1$–$C_4$-alkyl, OH, $C_6H_5$ or $C_6H_5CH_2$; and $R_1$, $R_2$, $R_3$, $R''_4$, $R_5$ and $R_6$ are such that at least one of the following two conditions A and B are complied with:

(A) at least one of the $R_1$, $R_2$, $R_3$, $R''_4$, $R_5$ and $R_6$ is different from H and (B) R″$_4$ is different from NO$_2$ when R$_1$=R$_2$=R$_3$=R$_5$=R$_6$=H] and acid addition salts thereof.

Among the interesting products of formula I which were mentioned hereinabove, the preferred compounds are those where R$_4$ is different from NO$_2$ and advantageously represents an NH$_2$ group. In fact, it has been observed that, although at low dose the nitro derivatives of formula I (where R$_4$=NO$_2$) have immunostimulant effects, they present undesirable cytotoxic effects at high dose. On the other hand, it has been observed in experiments that the compounds of formula I, where R$_4$ is different from NO$_2$ and advantageously represents in particular the group NH$_2$, do not have such cytotoxic effects.

The compounds of formula I may be prepared according to a method known per se by application of conventional reaction mechanisms. The method recommended according to the invention comprises the steps of:

(i) reacting a 2-halogeno-5-nitro-benzophenone of formula

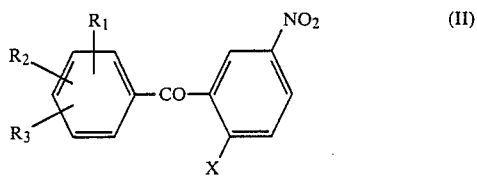

[in which R$_1$, R$_2$ and R$_3$ are defined as hereinabove and X represents an atom of halogen (preferably Cl or F to obtain high yields)], with a possibly substituted piperidine of formula:

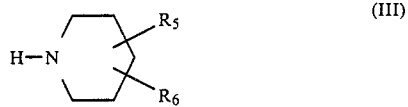

(in which R$_5$ and R$_6$ are defined as hereinabove), to obtain a nitro compound of formula:

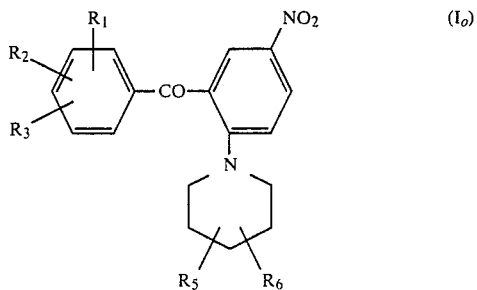

(ii) if necessary, submitting the compound Io thus obtained to a reduction reaction of the nitro group into amino group to obtain an amino derivative of formula I where R$_4$=NH$_2$, then, if need be, submitting said amino derivative to a reaction of deamination, to an alkylation or to a reaction of conversion of the amino group into halogen group.

The reaction of the 2-halogeno-5-nitro-benzophenone II with the piperidine III is preferably carried out in an organic solvent such as hydrocarbons (particularly aromatic hydrocarbons), ethers and alcohols, in the presence of an inorganic or organic base. In practice, one mole of II will be reacted with at least 1.1 mole of III at a temperature of between 15° C. and the reflux temperature of the reaction medium.

The reduction of the nitro group will be conducted in an organic solvent, preferably ethanol, in the presence of iron and concentrated hydrochloric acid (HCl 5N-12N) and at a temperature of between 15° C. and the boiling point of the solvent.

Deamination will be effected by diazotization of the amino group then substitution of the diazonium group by the atom of hydrogen in the presence of copper, at a temperature of between −20° C. and +20° C., and preferably at 0° C.

The diazonium group may also be replaced by an atom of chlorine or an atom of bromine under Sandmeyer's reaction conditions.

An amidification of the amino group will be effected by reaction of a compound of formula (I) where R$_4$=NH$_2$ with an alkyl or benzyl chloroformiate in an organic solvent, preferably an aromatic hydrocarbon, such as for example toluene, in the presence of an inorganic base, such as for example K$_2$CO$_3$ and at a temperature of between 0° C. and the boiling point of the solvent, and preferably at room temperature (15°-20° C.).

Alkylation of the amino group may be effected by reaction with an alkyl halide or according to Eschweiler-Clark's reaction in the case of a methylation.

Table I hereinafter shows as non-limiting examples a certain number of compounds of formula I which have been prepared according to the modi operandi referred to hereinabove.

Finally, the invention relates to a therapeutical composition, characterised in that it contains, in association with a physiologically acceptable excipient, at least one compound of formula I or one of its non-toxic acid addition salts, as immunostimulant and immunoadjuvant active ingredient.

Other advantages and features of the invention will be more readily understood on reading the following examples of preparation, which are in no way limiting, but are given by way of illustration.

PREPARATION I

[2-(4-methyl-1-piperidinyl)-5-nitrophenyl]-(4-chlorophenyl)-methanone (Example 1; Code No.: 399)

A mixture of 0.07 mole (20.7 g) of 2,4'-dichloro-5-nitrobenzophenone, of 0.1 mole (11.4 ml) of 4-methylpiperidine and of 10 g of K$_2$CO$_3$ in 100 ml of anhydrous ethanol is heated to reflux for 3 hours. After cooling of the reaction medium, the precipitate obtained is filtered, washed with water, dried then recrystallized from ethanol. 18 g (yield=71.7%) of the expected product are thus obtained. M.p.=136° C.

PREPARATION II

[2-(4-methyl-1-piperidinyl)-5-aminophenyl]-(4-chlorophenyl)-methanone (Example 2; Code No.: 442)

A mixture of 0.02 mole (7.2 g) of the product obtained according to preparation I above, 0.2 mole (11.2 g) of iron in powder form in 80 ml of a (90:10) v/v ethanol-water mixture and 4 ml of 10N hydrochloric acid, is taken to reflux for 2 hours. After cooling, the reaction medium is filtered, the filtrate is treated with 10N hydrochloric acid, the solvent is evaporated and the solid product thus obtained is washed with ethyl acetate, then placed in suspension in ethyl acetate. This suspension is treated with sodium bicarbonate and the organic phase is washed with water then dried and evaporated. 3.9 g of solid product are obtained, which give, after recrystallization from hexane, 2.9 g (yield=44%) of the expected product. M.p.=89° C.

Analysis: In the NMR spectrum of the product of Example 2 made at 80 MHz in CDCl$_3$, the following chemical displacements are observed (expressed in ppm): 0.70 (intensity=5); 1.37 (intensity=3); 2.50 and 2.80 (intensity=4); 3.58 (intensity=2); 6.80 (intensity=3); 7.35 and 7.70 (intensity=4).

PREPARATION III

[2-(4-methyl-1-piperidinyl)-5-(N-ethoxycarbonyl-amino)-phenyl]-(4-chlorophenyl)-methanone (Example 3; Code No.: 610)

Other nomenclature: Ethyl[3-(4-chlorobenzoyl)-4-(4-methyl-1-piperidinyl)-phenyl]-carbamate In an atmosphere of nitrogen, a mixture of 0.01 mole (3.3 g) of the product obtained according to preparation I, of 1.4 g of K$_2$CO$_3$ and of 0.1 mole (10.8 g) of ethyl chloroformiate in toluene is stirred at room temperature for 15 hours. The reaction medium is then diluted in water. The aqueous phase is extracted with ethyl acetate then the combined organic phases are washed with water then dried over magnesium sulphate. After evaporation of the solvent then recrystallization from hexane, 2.9 g (yield=72%) of the expected product are obtained. M.p.=132° C.

PREPARATION IV

[2-(4-methyl-1-piperidinyl)-phenyl]-phenyl-methanone (Example 4; Code No. 611)

0.01 mole (3 g) of [2-(4-methyl-1-piperidinyl)-5-aminophenyl]-phenyl-methanone (product of example 27; Code No. 592) is dissolved in ethanol. The mixture is cooled to 0° C. then 10 ml of sulphuric acid and 0.02 mole (1.4 g) of sodium nitrite are successively added. The mixture is stirred for 1 hour at 0° C. then allowed to return to room temperature (15°-20° C.). 0.65 g of activated copper is then added and the reaction medium is heated to 50° C. for 1 hour. After hydrolysis and neutralization, it is extracted with methylene chloride then washed with water. It is dried then the solvent is evaporated. By recrystallization from ethanol, 1 g (yield=37%) of the expected product is obtained. M.p.=82° C.

PREPARATION V

[2-(4-methyl-1-piperidinyl)-5-methylamino-phenyl]-(4-chlorophenyl)methanone (Example 6; Code No.: 613)

A mixture of 0.01 mole (4.8 g) of the product obtained according to the process of preparation VIII (Example 26) in hydrochloric ethanol (with HCl 5N) is taken to reflux for 5 hours. The ethanol is evaporated, the product obtained is rinsed with ethyl acetate then hydrolysed. After treatment with sodium hydroxide, extraction is carried out with ethyl acetate. One dries then the solvent is evaporated. The product obtained is purified over silica column (eluent: hexane-acetone). 2.5 g (yield=70%) of the expected product are obtained. M.p.=177° C.

PREPARATION VI

[2-(4-methyl-1-piperidinyl-5-chlorophenyl]-(4-chlorophenyl)-methanone (Example 22; Code No. 633)

The tetrafluoroborate of the diazonium of the product of Example 2 (prepared according to the process of preparation II hereinabove by reaction at 0° C. with sodium nitrite in tetrafluoroboric acid) is obtained. Then 0.02 mole (8.6 g) of this diazonium is added drop by drop to a solution of 2.75 g of cupric chloride in DMSO. The mixture is stirred for 30 mins., filtered then extracted with ethyl acetate. It is dried and the solvent is evaporated. [Concurrently with the expected product, the product of example 21 is formed (Code No. 634; m.p. 69° C.)]. After purification over silica column (eluent: benzene) of the residue of evaporation, 3 g (yield=40%) of the expected product are obtained. M.p.=109° C.

PREPARATION VII

[2-(4-methyl-1-piperidinyl)-5-(N-benzyloxycarbonyl-amino)-phenyl]-(4-chlorophenyl)-methanone (Example 25)

Other nomenclature: Benzyl[3-(4-chlorobenzoyl)-4-(4-methyl-1-piperidinyl)-phenyl]-carbamate By proceeding as indicated hereinabove in Preparation III from 0.02 mole (6.6 g) of the product of Example 2 (obtained according to Preparation II) and from 17 g of benzyl chloroformiate 6.6 g (yield=71%) of the expected product are obtained.

PREPARATION VIII

[2-(4-methyl-1-piperidinyl)-5-(N-benzyloxycarbonyl-N-methyl-amino)phenyl]-(4-chlorophenyl)-methanone (Example 26)

Other nomenclature: Benzyl[3-(4-chlorobenzoyl)-4-(4-methyl-1-piperidinyl)-phenyl]-N-methyl-carbamate In an atmosphere of nitrogen and at 0° C., 0.012 mole (0.3 g) of sodium hydride and 0.012 mole (5.5 g) of the product of Example 25 (obtained according to the process of Preparation VII) are stirred for 30 mins. in THF. 0.18 mole (2.6 g) of methyl iodide dissolved in THF are then added drop by drop. It is allowed to return to ambient temperature (15°-20° C.) and continues to be stirred for 15 hours. After hydrolysis of the reaction medium, the product is extracted with ethyl acetate then the organic phases are washed with water. After drying and evaporation of the solvent, 5 g (yield=85%) of the expected product are obtained.

The products of formula I according to the invention are useful in therapeutics as immunostimulant and immunoadjuvant agents. They are particularly indicated (i) in immunotherapy of cancers, (ii) as stimulants to antiviral and anti-infectious resistance and (iii) in the treatment of autoimmune diseases (rheumatoid polyarthritis, in particular).

The tests undertaken with the products according to the invention are summarized hereinbelow, particularly concerning (A) the stimulation of the lymphocytes of the mouse and (B) the toxicity.

A—Stimulation of the lymphocytes of the mouse

Lymphocytes ($5 \times 10^5$ cells per measurement) extracted from the spleen of inbred mice (DBA/2) are incubated for 36 hours at 37° C. in an atmosphere of oxygen with 5% of $CO_2$ in a culture medium (RPMI 1640) containing:

10% (by weight) of foetal calf serum (100 μl per measurement)

10 μl of a solution of lectins in the proportion of 5 μg/ml of phytohemaglutinine (PHA) and 40 μg/ml of Pokeweed Mitogen (PWM), and the substance to be tested.

The activity is evaluated by measuring the radioactivity obtained by incorporation in 24 hours of 2 μCi (i.e. $7.4 \times 10^4$ becquerels) of tritium-marked thymidine, with respect to a control culture.

The results obtained are grouped together in Table II hereinbelow which gives the optimum concentration of the products in μg/ml, and where symbols +, ++ and +++ signify:

+: stimulation of 0 to 50%
++: stimulation of 50% to 100%
+++: stimulation greater than 100%

B—Toxicity

The toxicity (LD-50 and LD-0) was determined by the i.p. route in the mouse according to the technique of S. T. Litchfield described in J. Pharm. Exp. Ther. 96, 99 (1949). The results obtained are shown in Table III hereinbelow.

Furthermore, the product of Example 2 (Code No. 442) was studied according to the delayed hypersensitivity test following the modus operandi described by P. H. Lagrange et al., J. Exp. Med. 139, 1529–1539 (1974). It has been observed that, at the single dose of 5 mg/kg per os administered in the mouse three days before sensitization, the product of Example 2 leads to a reduction by half of the delayed hypersensitivity.

The posology recommended in human therapy for the products according to the invention consists in administering by the oral route a daily dose of from 0.05 mg/kg to 1 mg/kg of a product of formula I for 7 days to 3 months.

TABLE 1

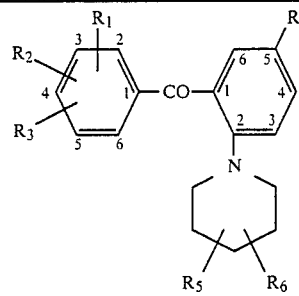

| Example | Code No. | $R_1$ | $R_2$ | $R_3$ | $R_4$ | $R_5$ | $R_6$ | M.p. (°C.)[b] |
|---|---|---|---|---|---|---|---|---|
| 1 | 399 | 4-Cl | H | H | $NO_2$ | 4-$CH_3$ | H | 136 |
| 2 | 442 | 4-Cl | H | H | $NH_2$ | 4-$CH_3$ | H | 89 |
| 3 | 610 | 4-Cl | H | H | $NHCO_2Et$ | 4-$CH_3$ | H | 132 |
| 4 | 611 | H | H | H | H | 4-$CH_3$ | H | 82 |
| 5 | 612 | 4-Cl | H | H | $N(CH_3)_2$ | 4-$CH_3$ | H | 99.5 |
| 6 | 613 | 4-Cl | H | H | $NHCH_3$ | 4-$CH_3$ | H | 117 |
| 7 | — | 3-Cl | H | H | $NH_2$ | 4-$CH_3$ | H | — |
| 8 | 747 | 2-Cl | H | H | $NH_2$ | 4-$CH_3$ | H | 94 |
| 9 | 697 | 3-$OCH_3$ | 4-$OCH_3$ | H | $NH_2$ | 4-$CH_3$ | H | 132 |
| 10 | — | 3-$OCH_3$ | 4-OH | H | $NH_2$ | 4-$CH_3$ | H | — |
| 11 | — | 3-$OCH_3$ | 4-$OCH_3$ | 5-$OCH_3$ | $NH_2$ | 4-$CH_3$ | H | — |
| 12 | 635 | 4-Cl | H | H | $NH_2$ | H | H | 96 |
| 13 | — | 4-OH | H | H | $NH_2$ | 4-$CH_3$ | H | — |
| 14 | 695 | 4-Cl | H | H | $NH_2$ | 3-$CH_3$ | H | 50 |
| 15 | 655 | 4-$CH_3$ | H | H | $NH_2$ | 4-$CH_3$ | H | 78 |
| 16 | 659 | 2-$CH_3$ | 4-$CH_3$ | H | $NH_2$ | 4-$CH_3$ | H | 90 |
| 17 | 660 | 4-F | H | H | $NH_2$ | 4-$CH_3$ | H | 116 |
| 18 | — | 4-$CF_3$ | H | H | $NH_2$ | 4-$CH_3$ | H | — |
| 19 | 637 | 4-Cl | H | H | $NH_2$ | 3-$CH_3$ | 5-$CH_3$ | 103 |
| 20 | 647 | 4-Cl | H | H | $NH_2$ | 2-$CH_3$ | H | 92 |
| 21 | 634 | 4-Cl | H | H | H | 4-$CH_3$ | H | 69 |
| 22 | 633 | 4-Cl | H | H | Cl | 4-$CH_3$ | H | 109 |
| 23 | 746 | 4-$OCH_3$ | H | H | $NH_2$ | 4-$CH_3$ | H | 64 |
| 24 | 704 | 4-$OCH_3$ | H | H | H | 4-$CH_3$ | H | (a) |
| 25 | — | 4-Cl | H | H | $NHCO_2CH_2C_6H_5$ | 4-$CH_3$ | H | — |
| 26 | — | 4-Cl | H | H | $N(CH_3)CO_2CH_2C_6H_5$ | 4-$CH_3$ | H | — |
| 27 | 592 | H | H | H | $NH_2$ | 4-$CH_3$ | H | 108 |
| 28 | 698 | 3-Cl | 4-Cl | H | $NH_2$ | 4-$CH_3$ | H | 94 |
| 29 | 727 | 3-$CH_3$ | 4-$CH_3$ | 5-$CH_3$ | $NH_2$ | 4-$CH_3$ | H | 127 |
| 30 | 736 | 4-Br | H | H | $NH_2$ | 4-$CH_3$ | H | 105 |
| 31 | 757 | 4-Cl | H | H | $NH_2$ | 4-$C(CH_3)_3$ | H | 109 |
| 32 | — | 4-Cl | H | H | $NH_2$ | 4-$C_2H_5$ | H | 92 |
| 33 | — | 4-Cl | H | H | $NH_2$ | 4-n-$C_4H_9$ | H | 103 |
| 34 | — | 4-Cl | H | H | $NH_2$ | 4-$CH_2C_6H_5$ | H | 109 |
| 35 | — | 4-Cl | H | H | $NH_2$ | 4-$C_6H_5$ | H | 144 |
| 36 | — | 4-Cl | H | H | $NH_2$ | 4-OH | H | 71 |
| 37 | — | 2-Cl | 4-Cl | H | $NH_2$ | 4-$CH_3$ | H | 117 |

Notes:
[a] oil $n_D^{20} = 1.5950$
[b] "M.p." means "Melting point"

TABLE II

Stimulation in vitro of mouse lymphocytes

| Example | Code No. | Optimal concentration (μg/ml) | Stimulation |
|---|---|---|---|
| 1 | 399 | 0.2 | ++ |
| 2 | 442 | 1 | +++ |
| 3 | 610 | 0.2 | ++ |
| 5 | 612 | 0.2 | + |
| 6 | 613 | 0.2 | + |
| 8 | 747 | 0.2 | + |
| 9 | 697 | 0.4 | + |
| 12 | 635 | 0.2 | + |
| 14 | 695 | 1 | ++ |
| 15 | 655 | 5 | ++ |
| 16 | 659 | 1 | ++ |
| 17 | 660 | 1 | + |
| 19 | 637 | 1 | ++ |
| 20 | 647 | 1 | +++ |
| 22 | 633 | 1 | + |
| 23 | 746 | 1 | ++ |
| 24 | 704 | 0.2 | + |
| 27 | 592 | 5 | + |
| 28 | 698 | 1.25 | ++ |
| 29 | 727 | 2.5 | + |

TABLE III

Toxicity

| Example | Code No. | Toxicity (i.p.) mouse (mg/kg) |
|---|---|---|
| 1 | 399 | LD −0 > 800 |
| 2 | 442 | LD −50 = 1300 |
| 3 | 610 | LD −0 > 800 |
| 4 | 611 | LD −0 > 800 |
| 5 | 612 | LD −0 > 800 |
| 6 | 613 | LD −0 > 800 |
| 8 | 747 | LD −0 > 800 |
| 9 | 697 | LD −0 > 800 |
| 12 | 635 | LD −0 > 800 |
| 15 | 655 | LD −0 > 800 |
| 16 | 659 | LD −50 = 750 |
| 17 | 660 | LD −0 > 800 |
| 19 | 637 | LD −0 > 800 |
| 20 | 647 | LD −0 > 800 |
| 21 | 634 | LD −50 = 1800 |
| 22 | 633 | LD −50 = 1800 |
| 23 | 746 | LD −0 > 800 |
| 24 | 704 | LD −0 > 800 |
| 27 | 592 | LD −0 > 800 |
| 28 | 698 | LD −0 > 800 |
| 29 | 727 | LD −0 > 800 |
| 30 | 736 | LD −0 > 800 |
| 31 | 757 | LD −0 > 800 |

What is claimed is:

1. A benzoyl-phenyl-piperidine derivative selected from the group consisting of:
(i) 2-piperidinobenzophenones of the formula

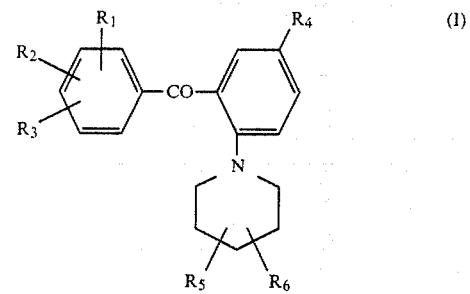

in which:
$R_1$, $R_2$ and $R_3$ are identical or different and each represents hydrogen, a hydroxy group, $CF_3$, a halogen, a lower alkyl group having 1 to 4 carbon atoms, or a lower alkoxy group having 1 to 4 carbon atoms;
$R_4$ represents $NH_2$;
$R_5$ and $R_6$ are identical or different and each represents hydrogen, a lower alkyl group having 1 to 4 carbon atoms, a hydroxy group, a phenyl group or a benzyl group; and
(ii) acid addition salts thereof.

2. A therapeutical composition which comprises, in association with a physiologically acceptable excipient, a pharmaceutically effective amount of a compound of formula (I) according to claim 1 or one of its non-toxic acid addition salts.

3. [2-(4-Methyl-1-piperidinyl)-5-aminophenyl]-(4-chloro-phenyl)methanone and acid addition salts thereof.

4. [2-(3-Methyl-1-piperidinyl)-5-aminophenyl]-(4-chloro-phenyl)methanone and acid addition salts thereof.

5. [2-(2-Methyl-1-piperidinyl)-5-aminophenyl]-(4-chloro-phenyl)methanone and acid addition salts thereof.

* * * * *